(12) United States Patent
Huh

(10) Patent No.: US 11,931,831 B2
(45) Date of Patent: Mar. 19, 2024

(54) STATUS ALARM MASK FOR WELDING AND METHOD OF OPERATING STATUS ALARM MASK

(71) Applicant: OTOS WING.CO., LTD., Seoul (KR)

(72) Inventor: Moon Young Huh, Seoul (KR)

(73) Assignee: OTOS WING.CO., LTD., Seoul (KR)

( * ) Notice: Subject to any disclaimer, the term of this patent is extended or adjusted under 35 U.S.C. 154(b) by 468 days.

(21) Appl. No.: 16/358,208

(22) Filed: Mar. 19, 2019

(65) Prior Publication Data
US 2019/0321904 A1 Oct. 24, 2019

(30) Foreign Application Priority Data

Apr. 24, 2018 (KR) .......................... 10-2018-0047317

(51) Int. Cl.
*B23K 9/095* (2006.01)
*B23K 31/12* (2006.01)
*G05B 19/406* (2006.01)

(52) U.S. Cl.
CPC .......... *B23K 9/0953* (2013.01); *B23K 9/0956* (2013.01); *B23K 31/125* (2013.01); *G05B 19/406* (2013.01); *G05B 2219/45135* (2013.01)

(58) Field of Classification Search
CPC .. B23K 9/0953; B23K 9/0956; B23K 31/125; B23K 37/006; B23K 9/322; G05B 19/406; G05B 2219/45135; A61F 9/06; A61F 9/065; F16P 1/06; G08B 21/18
See application file for complete search history.

(56) References Cited

U.S. PATENT DOCUMENTS

| | | | | |
|---|---|---|---|---|
| 6,734,393 B1* | 5/2004 | Friedl | ..................... | A61F 9/067 219/130.01 |
| 6,930,280 B2* | 8/2005 | Zauner | ................. | B23K 9/0953 219/130.5 |
| 7,962,967 B2* | 6/2011 | Becker | ...................... | A61F 9/06 2/8.1 |

(Continued)

OTHER PUBLICATIONS

Office Action dated Apr. 2, 2019 in Korean Patent Application No. 10-2018-0047317, all pages.

(Continued)

*Primary Examiner* — Janie M Loeppke
*Assistant Examiner* — Abigail H Rhue
(74) *Attorney, Agent, or Firm* — Kilpatrick Townsend & Stockton LLP

(57) ABSTRACT

A status alarm mask may include a main body to cover a face and eyes of a user. The mask may include a filter unit placed at a front surface portion of the main body to protect the eyes. The mask may include a communication module configured to establish a communication session with a welding torch held by the user and receive at least one inclination value of the welding torch being operated by the user, through the communication session. The mask may include a controller configured to determine whether a work of the torch is in progress, on the basis of an operation of the filter unit and to generate notification output data when the work of the torch is in progress. The mask may include an output unit placed at a location not overlapping with the filter unit and configured to receive and output the notification output data.

12 Claims, 7 Drawing Sheets

(56) References Cited

U.S. PATENT DOCUMENTS

| | | | |
|---|---|---|---|
| 8,680,434 B2* | 3/2014 | Stoger | B23K 9/0956 219/137.7 |
| 2008/0158502 A1 | 7/2008 | Becker et al. | |
| 2008/0314887 A1 | 12/2008 | Stoger et al. | |
| 2009/0276930 A1 | 11/2009 | Becker et al. | |
| 2011/0248864 A1 | 10/2011 | Becker et al. | |
| 2012/0273473 A1* | 11/2012 | Zhang | B23K 9/091 219/130.31 |
| 2015/0246406 A1* | 9/2015 | Takayama | B23K 9/32 219/124.1 |

OTHER PUBLICATIONS

Preliminary Search Report and Written Opinion for French Patent Application No. 1903394 dated Apr. 3, 2020.

* cited by examiner

STATUS ALARM MASK FOR WELDING AND METHOD OF OPERATING STATUS ALARM MASK

CROSS-REFERENCE TO RELATED APPLICATION

This application claims the benefit of Korean Patent Application No. 10-2018-0047317, filed on Apr. 24, 2018, in the Korean Intellectual Property Office, the disclosure of which is incorporated herein in its entirety by reference.

BACKGROUND

1. Field

One or more embodiments relate to a status alarm mask for welding and a method of operating the status alarm mask.

2. Description of the Related Art

Workers wear protective equipment that protect them from light, high heat, and the like generated during welding such as arc welding. However, workers can only confirm welding progression through protective equipment when worn, and thus there are inconveniences such as removal of protective equipment to confirm various pieces of information for welding, such as conditions set in a welding apparatus, and visual confirmation of the information.

SUMMARY

Therefore, the present disclosure has been made to address the above-described problems and/or limitations, and one or more embodiments include output data corresponding to an event, provided by monitoring an inclination value of a torch of a user and receiving an event outside a normal range.

One or more embodiments include corresponding output data provided by inferring a welding status of a current work by using the inclination value of a torch of a user.

Additional aspects will be set forth in part in the description which follows and, in part, will be apparent from the description, or may be learned by practice of the presented embodiments.

According to one or more embodiments, a status alarm mask includes: a communication module configured to receive an inclination value of a welding torch being operated by a user, through communication with the welding torch; a controller configured to generate notification output data in consideration of whether a current work is in progress and the inclination value of the torch; and an output unit configured to output the notification output data corresponding to the inclination value of the welding torch.

According to one or more embodiments, a status alarm mask includes: a communication module configured to establish a communication session with a welding torch and receive an inclination value of a welding torch being operated by a user through the communication session; a controller configured to generate whether the inclination value exceeds a normal range, in consideration of whether a work is in progress and the inclination value of the welding torch; and an output unit configured to output notification output data notifying whether the inclination value exceeds the normal range.

According to the present embodiments, the controller may update the normal range of the current work on the basis of a set of inclination values acquired at a first time interval and set the normal range of the current work as a reference value of the welding torch.

According to the present embodiments, when an inclination value outside the normal range is received from the welding torch, the controller may generate notification output data corresponding to the inclination value.

According to the present embodiments, the controller may be configured to generate first notification output data in accordance with a first event at which the inclination value outside the normal range is received and output the first notification output data via the output unit, and when an inclination value having received for a predetermined period of first time or more is not within the normal range after the first event occurs, the controller may be configured to generate second notification output data and output the second notification output data via the output unit for a predetermined time interval.

According to the present embodiments, the first notification output data or the second notification output data may be set to be output via at least one of an LED, a vibration module, and a speaker.

According to the present embodiments, the controller may be configured to generate notification output data in accordance with a second event at which the inclination value outside the normal range is received and output the notification output data via the output unit, and when an inclination value having been received for a predetermined period of second time or more is outside the normal range after the second event occurs, the controller may be configured to change a temperature of the welding torch to a preset minimum temperature or less.

A computer program according to an embodiment may be stored in a medium using a computer to perform any one of methods of operating a status alarm mask, according to embodiments.

One or more embodiments also provide other methods and systems for implementing the present disclosure, and a computer-readable recording medium for recording a computer program for executing the above-described method.

Other aspects, features, and advantages other than those described above will become apparent from the accompanied drawings, the following claims, and the detailed description.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
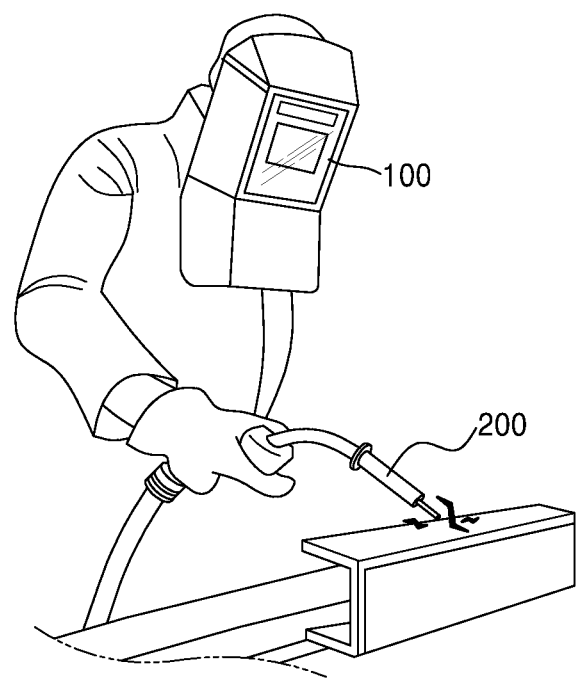
FIG. 1 is a view for explaining a structure of a monitoring system according to embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Since various modifications may be made in the present disclosure and the present disclosure may have various embodiments, particular embodiments are illustrated in the accompanying drawings and will be described in detail in the detailed description. Effects and features of the present disclosure, and methods of achieving them will become apparent from embodiments, which will be described below in detail, with reference to the accompanying drawings. However, the embodiments set forth herein are not intended to limit the present disclosure and may be embodied in various forms.

FIG. 1 is a view for explaining a structure of a monitoring system according to embodiments.

The monitoring system may include a welding torch 200 and a status alarm mask 100 and may determine quality and performance rating of current welding on the basis of torch inclination values obtained through the welding torch 200. The welding torch 200 is connected to the status alarm mask 100 via a communication network such that data is mutually received and transmitted. Referring to FIG. 1, the status alarm mask 100 and the welding torch 200 are operated in one-to-one correspondence, but the present disclosure is not limited thereto. That is, one-to-n correspondence is possible. In other words, one status alarm mask 100 may be connected to n welding torches 200. In addition, n status alarm masks 100 may be connected to one welding torch 200.

The welding torch 200 performs real-time sensing on an inclination value thereof. The welding torch 200 may set a time interval for monitoring the inclination value and set the time interval to a monitoring mode. In the monitoring mode, the welding torch 200 may monitor the inclination value thereof. The welding torch 200 may perform a function of setting a reference value of a current work and setting the reference value to a setting mode for sensing the inclination value. In the setting mode, the welding torch 200 may set a reference value for the inclination values of a current work.

The status alarm mask 100 may monitor an inclination of an external welding torch and provide a user with monitoring data for the inclination through visual and tactile means. The status alarm mask 100 may monitor statuses of a plurality of welding torches by receiving inclination values of the welding torches. The statuses of the welding torches may be output simultaneously, but may be output in various manners without being limited thereto. The status alarm mask 100 may be configured to provide monitoring data for the inclination of the corresponding welding torch in accordance with each split time interval obtained by dividing a first time interval by the number of welding torches. For example, the status alarm mask 100 may sequentially output status values of a plurality of welding torches. Time intervals corresponding to the plurality of welding torches may be set, and a status value of the corresponding welding torch at each time interval may be output. At this time, to prevent collision of received data between welding torches, the status alarm mask 100 may be configured to first receive identification information of the welding torches in accordance with each split time interval. Status values of the welding torches may be transmitted using the time interval assigned to each welding torch. The status alarm mask 100 may receive and output the received status values and the identification information of welding torches.

In addition, when changes in inclination of the welding torches 200 are sensed, the sensed inclination values may be transmitted to the status alarm mask 100. In this case, the status alarm mask 100 identifies a torch corresponding to the inclination value by using identification information included in the received packet. The status alarm mask 100 may visually output monitoring data of a plurality of welding torches.

The status alarm mask 100 may receive an operation mode and an inclination value from the welding torch 200 via a communication network. The status alarm mask 100 differently processes the inclination values according to the operation mode. When the operation mode is set as a setting mode, the status alarm mask 100 determines a normal range by using the inclination value. When the operation mode is set as a monitoring mode, the status alarm mask 100 may output whether the inclination value is within the normal range by comparing the inclination value with the normal range. When the normal range is not set, the status alarm mask 100 may generate visual data by tracking movements, patterns, and the like in which the inclination value changes. In this case, the status alarm mask 100 may determine whether a difference between a previous inclination value and a current inclination value is a predetermined threshold difference value or greater. The status alarm mask 100 outputs the inclination value and notification output data including monitoring data for the corresponding inclination value. The notification output data may be in various forms such as light, a vibration, a message, and the like. In this regard, the monitoring data for the inclination value may include whether the inclination value is within the preset normal range and/or exceeds the normal range. In addition, the monitoring data for the inclination value may include a value, a grade, a level, and the like that correspond to the inclination value of a torch. In this regard, the inclination value may be determined on the basis of a reference plane. The reference plane may be the ground, a plane perpendicular to the ground, a plane set by a user, or the like.

In an additional embodiment, the status alarm mask 100 may use a sensing value to set whether to stop a work, to progress a work, an operation mode, and the like. The status alarm mask 100 may sense a motion, a voice, or the like of a user, thereby determining that a work is stopped. The status alarm mask 100 may change the operation mode of a welding torch by sensing a fine motion or voice, or the like of a user. When the inclination of a welding torch is outside a predetermined range, for example, a range between 10° and 80°, the operation mode of the welding torch may be switched from the setting mode to the monitoring mode, or from the monitoring mode to the setting mode. This may prevent continuous generation of the notification output data even when the work is stopped.

In another embodiment, the status alarm mask 100 may acquire an inclination value of the welding torch 200 through image sensing included therein in a state in which the status alarm mask 100 is unable to smoothly communicate with the welding torch 200. The status alarm mask 100 may transmit the sensed image data to an external server and receive the inclination value of the welding torch 200 in response thereto.

According to the present embodiment, the welding torch 200 may include a mode setting unit configured to set the operation mode as a setting mode or a monitoring mode. The welding torch 200 may sense the inclination value thereof. According to the present embodiment, the welding torch 200 is connected to the status alarm mask 100 via a communication network, and transmits the operation mode and the inclination value thereto. The welding torch 200 may receive a control signal for controlling a temperature, power, or the like of the welding torch 200 from the status alarm mask 100. In a further embodiment, the welding torch 200 may be controlled by a motion of a user, or in accordance with a control signal from the status alarm mask 100 when predetermined conditions are satisfied.

Figure 2:
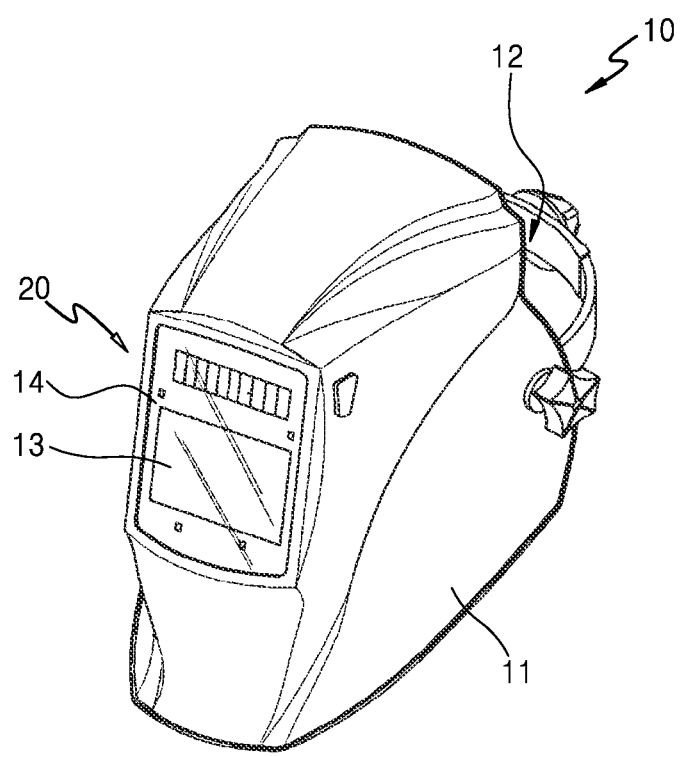
FIG. 2 is a schematic perspective view of a status alarm mask according to an embodiment.

FIG. 2 is a schematic perspective view of a status alarm mask 10 according to an embodiment.

Referring to FIG. 2, the status alarm mask 10 may include a main body 11 configured to protect the face and eyes of a user and a fixing portion 12 placed at a rear surface of the main body 11 and configured to fix the status alarm mask 10 to a head part of the user. The main body 11 may be made of a material with predetermined strength, for example, reinforced plastic or the like, but the present disclosure is not limited thereto, and any material capable of being resistant to factors that may occur during welding, such as sparks, may be variously used. The fixing portion 12 is a component that is in direct contact with the head part of a user, and a side surface of the fixing portion 12, i.e., at least a portion of an inner side surface of the fixing portion 12, which is in direct contact with the head part of a user, may include a fibrous material or a soft material such as a cushioning material.

The main body 11 is a main portion of the status alarm mask 10, and a blackened filter unit 13 may be located at a front surface 20 of the main body 11.

The blackened filter unit 13 may protect the eyes of a user by blocking welding light generated during welding. The blackened filter unit 13 may include, for example, a liquid crystal display (LCD) panel in which the degree of blackening is adjustable in accordance with an alignment direction of liquid crystals. In one embodiment, the degree of blackening of the blackened filter unit 13 may be manually adjusted in accordance with selection (request) of a user. In another embodiment, the degree of blackening of the blackened filter unit 13 may be automatically adjusted according to the brightness of welding light. When the degree of blackening of the blackened filter unit 13 is automatically adjusted according to the brightness of welding light, a first optical sensor 14 may be used. For example, when the first optical sensor 14 senses the intensity of strong welding light and transmits an electrical signal for the sensed intensity of welding light to a controller, which will be described below, the controller may control the degree of blackening of the blackened filter unit 13 on the basis of the intensity of the welding light. As illustrated in FIG. 2, the first optical sensor 14 is located at the front surface of the main body 11 and in the vicinity of the blackened filter unit 13.

Figure 3:
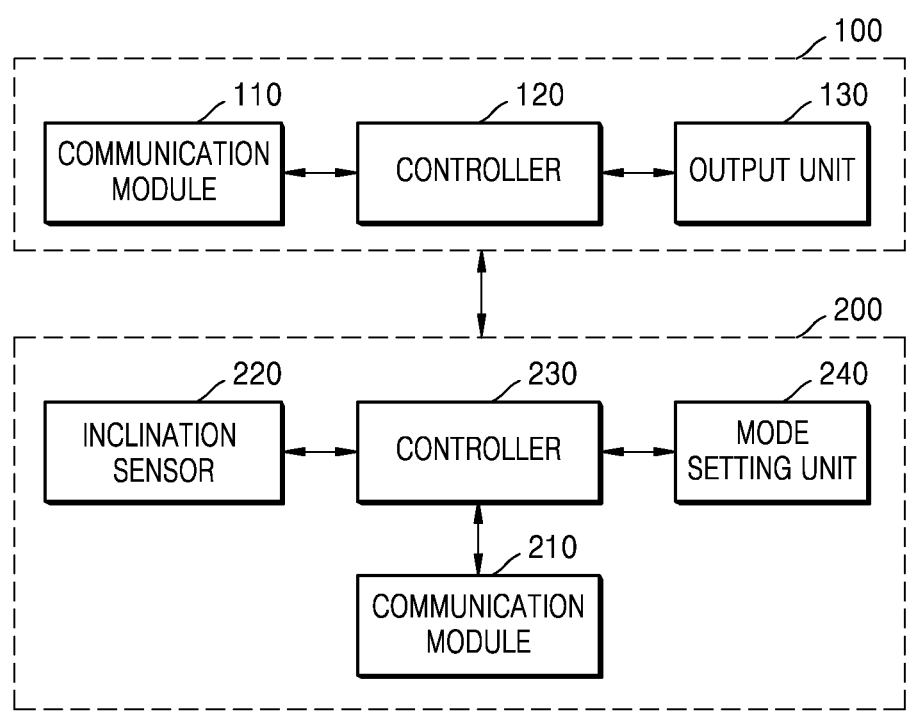
FIG. 3 is a block diagram illustrating structures of a status alarm mask and a welding torch, according to embodiments.

FIG. 3 is a block diagram illustrating structures of the status alarm mask 100 and the welding torch 200, according to embodiments.

The status alarm mask 100 may include a communication module 110, a controller 120, and an output unit 130, together with a main body and a filter unit.

The communication module 110 sets a communication session configured to receive/transmit data from/to the welding torch 200. The communication module 110 may include a module capable of implementing short range wireless communication (e.g., Bluetooth, Wi-Fi, and Wi-Fi Direct), long range wireless communication (3G and high-speed downlink packet access (HADPA)), or long term evolution (LTE).

The controller 120 performs a control operation to process the inclination value of the welding torch 200 according to the operation mode received by the welding torch 200. The controller 120 generates the inclination value and notification output data including monitoring data for the corresponding inclination value and outputs them via the output unit 130. The controller 120 may include a memory (cache, flash, disk, or the like) configured to store received data or store output data.

The controller 120 may determine whether a work of the torch is in progress on the basis of an operation of a filter unit. Optionally, the controller 120 may determine whether the work of the torch progresses based on the at least one inclination value. The controller 120 may generate notification output data including monitoring data for at least one inclination value when the work of the torch is in progress. The controller 120 may determine whether the work of the torch is in progress according to whether welding light has been received via the filter unit. The controller 120 may determine whether the work of the torch is in progress on the basis of the intensity of light having been received via an optical sensor.

The controller 120 may update a normal range of a current work on the basis of a set of inclination values obtained at a first time interval. The first time interval may be determined according to a time point of a work, a time at which mode is changed, or the like. The first time interval may be determined based on a time point when the welding torch is supplied with power or a time point when a monitoring mode switches to a setting mode. The normal range may vary according to each work. The normal range may vary depending on welding performed via each operation. In a further embodiment, the controller 120 may perform a function of setting the normal range of the current operation as a reference value of the welding torch 200. The welding torch 200 may set the received normal range as a reference value and transmit the inclination value to the status alarm mask 100 only when a difference from the reference value is greater than a predetermined difference value. In this regard, the reference value of the inclination value may be set by the status alarm mask 100.

The controller 120 is configured to generate first notification output data in accordance with a first event at which an inclination value outside the normal range is received and output the first notification output data via the output unit 130. In this regard, the first notification output data is output in accordance with the sensed time point, and an output time interval of the first notification output data may be in accordance with setting of a user. The controller 120 may additionally generate second notification output data and output the data via the output unit 130, when the received inclination value does not return to be within the normal range even when first predetermined time elapses after the first event occurs, i.e., when an inclination outside the normal range is continuously sensed. At this time, the first and second notification output data are set to be output via at least one of an LED, a vibration module, and a speaker and may be output in different manners. The controller 120 may output the inclination value by a method such as light, vibration, or the like.

The controller 120 may generate notification output data in accordance with a second event at which an inclination value outside the normal range is received to be output via the output unit 130 and may change a temperature of the torch to a predetermined minimum temperature or less when the received inclination value is outside the normal range during a predetermined period of second time or more after the second event occurs.

The controller 120 may generate and provide guide information so that the inclination of the torch is within the normal range, when a change in the inclination outside the normal range is sensed by an inclination sensor of the welding torch 200.

The controller 120 may change welding ability information of a user on the basis of a set of inclination values of current welding and the notification output data. The controller 120 may update the current welding ability information through combination of a set of inclination values of a user and previous welding ability information. The controller 120 may generate welding ability information of each user on the basis of an inclination value of a monitored torch, welding time information, and the like, and manage the welding ability information of each user. The controller 120 performs a scheduling function such that a work in accordance with welding ability of each user is assigned.

The welding torch 200 may include a communication module 210, an inclination sensor 220, a controller 230, and a mode setting unit 240.

The communication module 210 receives/transmits data from/to the status alarm mask 100. The communication module 210 may include a module capable of implementing short range wireless communication (e.g., Bluetooth, Wi-Fi, and Wi-Fi Direct), long range wireless communication (3G and high-speed downlink packet access (HADPA)), or long term evolution (LTE).

The inclination sensor 220 performs a function of measuring an inclination value of a torch. In a further embodiment, the inclination sensor 220 may utilize the inclination value of a torch as an ON/OFF switch such as a power supply of a heating unit included in the torch. The inclination sensor 220 may turn off the torch when the inclination value of the torch is outside a predetermined normal range.

The controller 230 may control operations of the communication module 210, the inclination sensor 220, and the mode setting unit 240. The controller 230 may transmit values set by the inclination sensor 220 or the mode setting unit 240 to a status alarm mask.

The mode setting unit 240 may set an operation mode of a welding torch in response to a user input. The mode setting unit 240 may be operated in an ON/OFF manner, and particularly, may switch to a setting mode when the mode setting unit 240 is ON and switch to a monitoring mode when the mode setting unit 240 is OFF.

The mode setting unit 240 may include a first mode setting unit configured to set the operation mode of the welding torch to a setting mode and a second mode setting unit configured to set the operation mode of the welding torch to a monitoring mode. The operation mode of the welding torch may be set as a setting mode by the first mode setting unit, and the operation mode of the welding torch may be set as a monitoring mode by the second mode setting unit.

Figure 4:
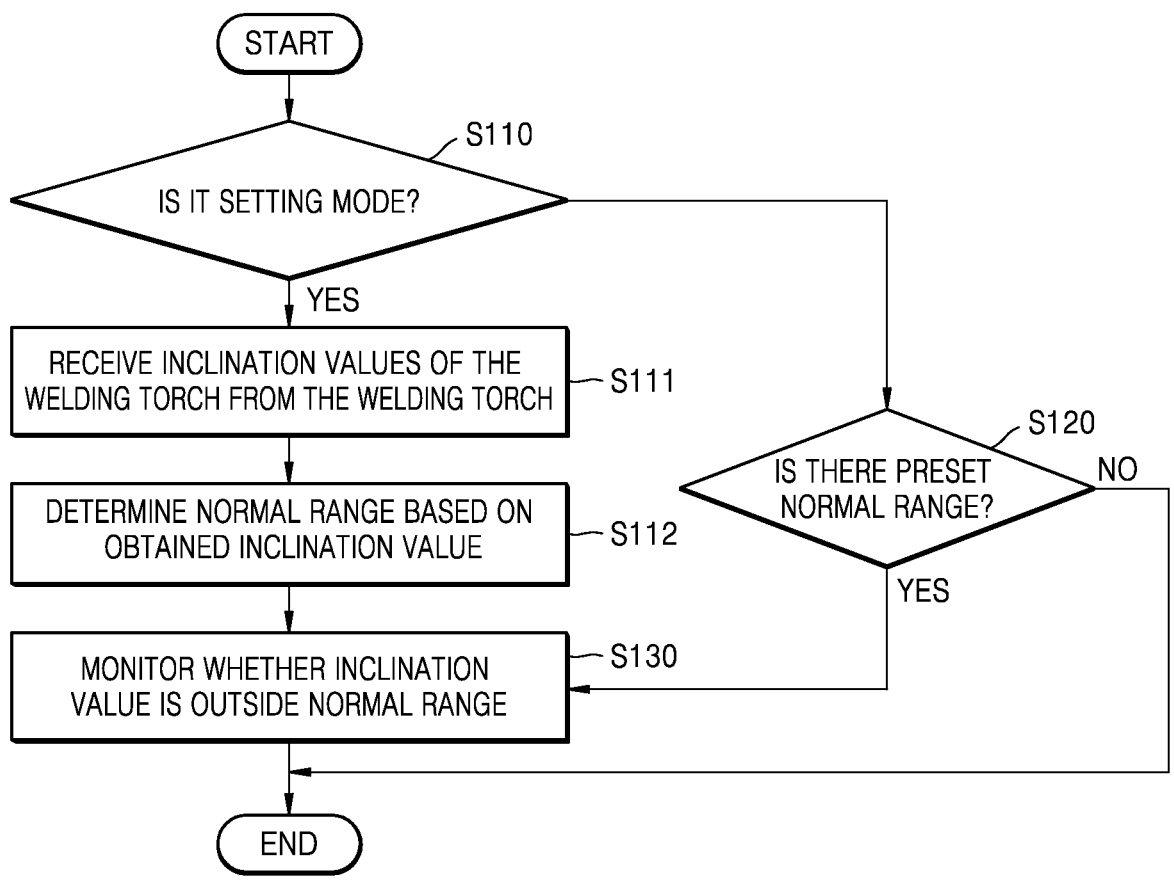
FIGS. 4 and 5 are flowcharts illustrating a method of monitoring welding quality, according to embodiments.
Figure 5:
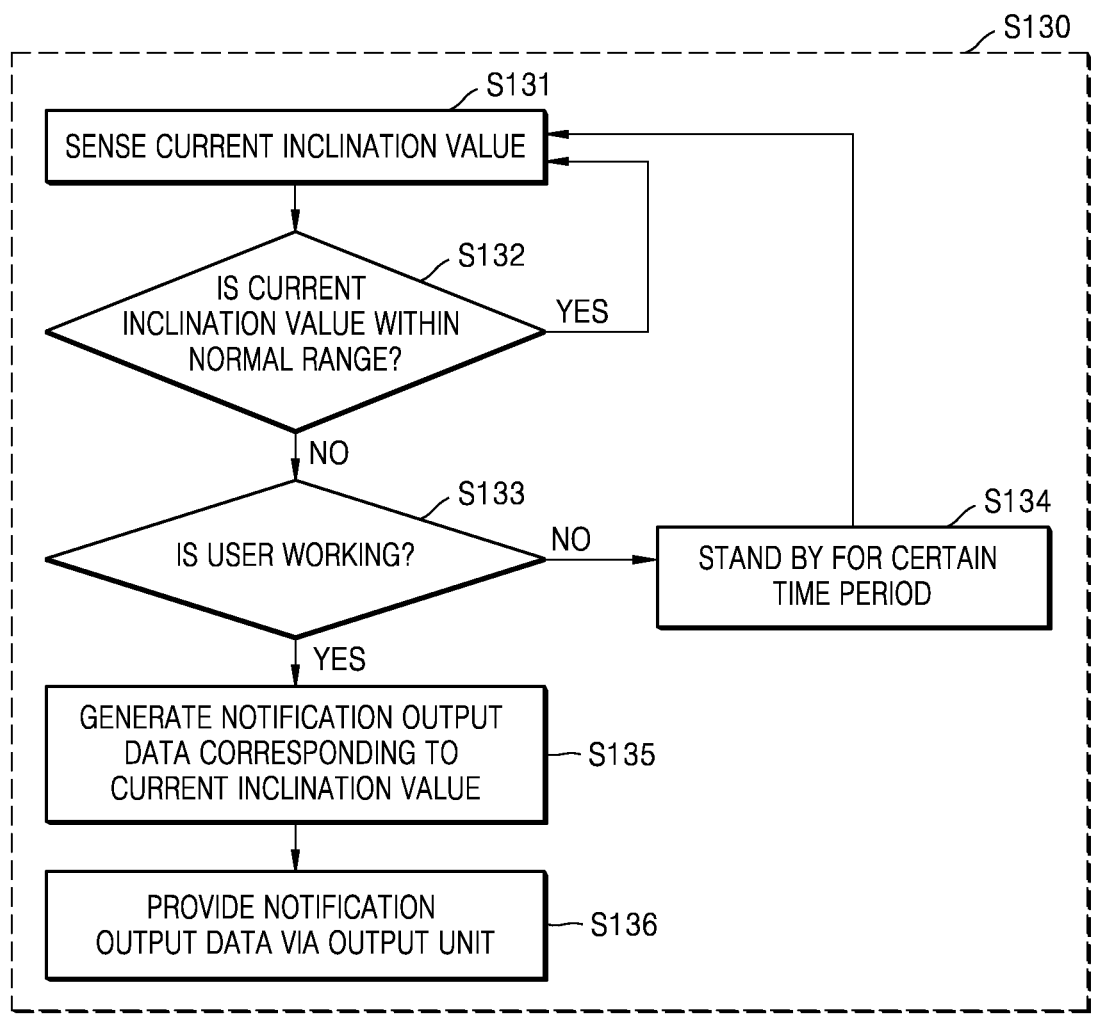

FIGS. 4 and 5 are flowcharts illustrating a method of monitoring welding quality, according to embodiments. The flowchart of FIG. 4 illustrates a process of setting a reference value of an inclination, wherein the setting process is performed by an apparatus for monitoring welding quality.

The apparatus for monitoring welding quality may receive a value of an operation mode of a welding torch from the welding torch and determine whether the operation mode is a setting mode (operation S110).

The status alarm mask 100 receives inclination values of the welding torch from the welding torch when the operation mode is a setting mode (operation S111). The welding torch may sense inclination values of the welding torch in a first mode during a predetermined period of time. The obtained inclination values or packetized inclination values are transmitted to the status alarm mask 100. At this time, the welding torch may monitor a case in which a change in the inclination value is sensed and update the inclination value when the change in the inclination value is sensed.

Next, the status alarm mask 100 may determine whether there is a preset normal range when the operation mode is a setting mode (operation S120). If the normal range is not set, the status alarm mask 100 may intermittently update the inclination value of the welding torch, which is received from the welding torch.

The status alarm mask 100 changes the normal range by using the obtained inclination value (operation S112). The normal range may be set according to the inclination value (s) of the welding torch that has/have been input in the setting mode and may be used to evaluate welding quality. The normal range may be set differently depending on the degree of difficulty or the type of a work being currently performed for welding, or the like.

The status alarm mask 100 may monitor whether the received inclination value of the welding torch is outside the normal range (operation S130). The status alarm mask 100 may monitor an inclination of an external welding torch and generate monitoring data for the inclination.

Through the above-described processes, the status alarm mask 100 may set a normal range of current welding on the basis of inclination values of the welding torch that have been sensed in the setting mode. The set normal range may be used to determine welding quality.

FIG. 5 is a flowchart for explaining operation S130.

The status alarm mask 100 receives a current inclination value from the welding torch (operation S131).

The status alarm mask 100 may monitor an inclination of an external welding torch and generate monitoring data for the inclination. In particular, the status alarm mask 100 determines whether the current inclination value is within a preset normal range (operation S132). The controller 120 may determine whether a work of the torch is in progress on the basis of an operation of a filter unit. The controller 120 may generate notification output data including monitoring data for at least one inclination value when the work of the torch is in progress. The controller 120 may determine whether the work of the torch is in progress according to whether welding light has been received via the filter unit. The controller 120 may determine whether the work of the torch is in progress on the basis of the intensity of light having been received via an optical sensor.

When the inclination value is within the preset normal range, the status alarm mask 100 may continuously monitor the inclination value of the welding torch. The status alarm mask 100 determines whether a user's work is in progress when it is determined that the current inclination value is outside the preset normal range. At this time, whether the work is in progress may be acquired via a sensor included in the status alarm mask 100. For example, when a temperature value of the welding torch is a preset temperature value or greater, it may be determined whether light corresponding to welding is included on the basis of brightness information of respective pixels of an image, and when light corresponding to welding is included, the case may be determined as "in progress". The status alarm mask 100 generates notification output data corresponding to the current inclination value when the work of the torch is in progress (operation S135). At this time, the status alarm mask 100 may be configured to divide 0° to 90° into 10-degree unit sections and output notification output data corresponding to each section. The status alarm mask 100 may divide sections by a predetermined unit, for example, a 1-degree unit, on the basis of the reference value of the inclination and output notification output data corresponding to each section. The notification output data may also be provided by corresponding to comparison data between the current inclination value and the normal range, or may be provided by corresponding to the current inclination value itself.

The status alarm mask 100 provides the notification output data via an output unit (operation S136). The notification output data may be set to be output by turning on warning light, generating vibration, or outputting a message. The output unit may be included in the status alarm mask 100, but may also be included in a separate electronic device.

The status alarm mask 100 controls warning light to be turned on in accordance with time when the inclination value of the welding torch exceeds the normal range. The status alarm mask 100 may further include an output unit configured to output text, generate light, generate vibration, or the like. The status alarm mask 100 may use text to notify a user that the inclination value is outside the normal range. The status alarm mask 100 may generate a vibration to notify a user that the inclination value is outside the normal range. At this time, warning light may be turned on continuously or periodically during a period of time when the inclination value of the welding torch exceeds the normal range, and the warning light may be turned off when the inclination value of the welding torch returns to the normal range.

When a time, which has elapsed after the inclination value exceeds the normal range, is outside a certain preset time, the status alarm mask 100 may cause a welding job of the connected welding torch to be stopped. In this case, the status alarm mask 100 may perform a control operation such that a temperature of the welding torch is changed to a predetermined temperature or less. The status alarm mask 100 may perform a control operation such that power to be transmitted to a heating unit of the welding torch is blocked, to lower the temperature of the welding torch. Even though power to be transmitted to the heating unit of the welding torch is blocked, power is transmitted to a communication module and/or a controller of the welding torch.

When the work of the torch is not in progress, the status alarm mask 100 may stop the function of sensing the current inclination value for a certain period of time. The status alarm mask 100 may stop a process of acquiring inclination values of the welding torch. The status alarm mask 100 may stop the acquisition of inclination values by transmitting a control signal. The status alarm mask 100 stops the function of monitoring an inclination for a predetermined period of time and stands by (operation S134).

In other embodiments, the status alarm mask 100 may receive an inclination value of a welding torch and provide an alarm therefor. When the inclination value of the welding torch is not received, the status alarm mask 100 may determine welding quality of a user by using image data obtained by photographing the welding torch. When a rapid change in the inclination of the welding torch, for example, a change therein by 10% or more of the previous inclination (the inclination value is 0.9 or less or 1.1 or more of the previous inclination) is sensed, welding quality at the corresponding time may be determined to be unsuitable.

In other embodiments, the status alarm mask 100 may further include an image sensor configured to acquire a welding image of a work done by a user. The status alarm mask 100 may analyze the welding image and generate a change in the inclination of the welding torch. When the change in the inclination of the welding torch is sensed, the status alarm mask 100 may turn on a warning light in accordance with the time at which the change is sensed or the change occurs. The status alarm mask 100 may be controlled to continuously turn on a warning light unless a change in which the inclination of the welding torch is restored to the previous state is detected. Information provided by the warning light varies depending on the color, lighting pattern, cycle, or the like of the warning light. The output unit such as a warning light may be included in the status alarm mask 100, or may be included in a part of the welding torch. The status alarm mask 100 may output a change in the inclination of the welding torch by vibration, a message, or the like through an external electronic device when the operation of the output unit malfunctions. At this time, the status alarm mask 100 may output information corresponding to the inclination of the torch, such as vibration, a warning light, a message, or the like through an external electronic device having undergone a registration process.

Figure 6:
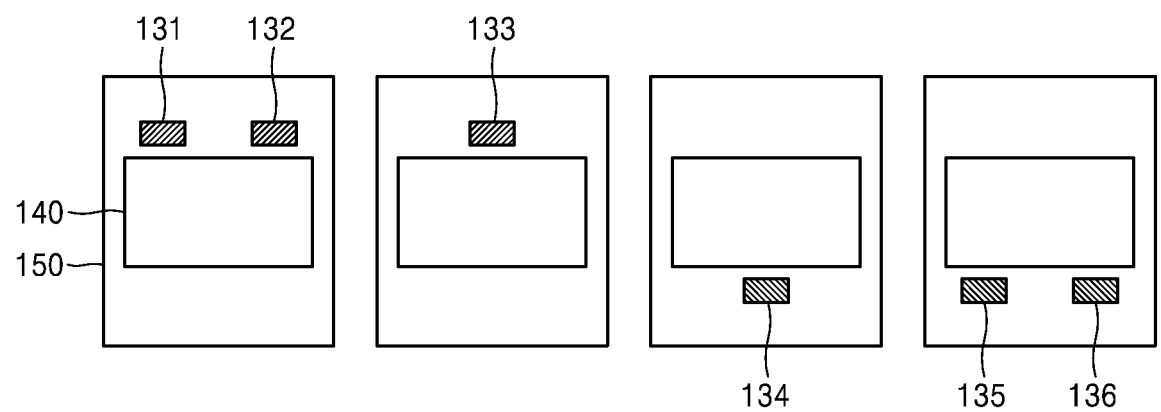
FIG. 6 is view for explaining embodiments of the present disclosure.

As illustrated in FIG. 6, the status alarm mask 100 may include an output unit at a position where the output unit is recognizable by a user in a mask. The status alarm mask 100 may include two output units proximate upper or lower ends of a permeable surface 140 through which a front surface is visible. A first output unit 131 or 135 may output whether the received inclination value exceeds the normal range, and a second output unit 132 or 136 may output whether the received inclination value is within the normal range. First and second output units may be restored to the original state after predetermined time elapses after output.

The status alarm mask 100 may include a single output unit at an upper or lower end of a permeable surface. An output unit 133 or 134 may alternatively output whether the inclination value exceeds the normal range or whether the inclination value is within the normal range.

The status alarm mask 100 may output the inclination value of the welding torch by light as illustrated in FIG. 6, but may also output the inclination value of the welding torch using various methods such as vibration, text, or the like. The status alarm mask 100 may output whether the inclination value of the welding torch satisfies specific conditions as TRUE or FALSE. The status alarm mask 100 may include an output unit configured to perform an output operation in accordance with TRUE, or output units configured to respectively perform output operations in accordance with TRUE and FALSE.

The output unit of the status alarm mask 100 may be located at a position that does not interfere with the user's vision, such as on the forehead, behind the head, or the like, and thus may inform a user of the inclination value of the torch and whether the inclination value exceeds the normal range. The output unit may be controlled to output at an output frequency different from that of a permeable surface. The output unit, the first output unit, and the second output unit may be one of an LED light, a vibration module, a display panel, and a speaker.

Figure 7A:
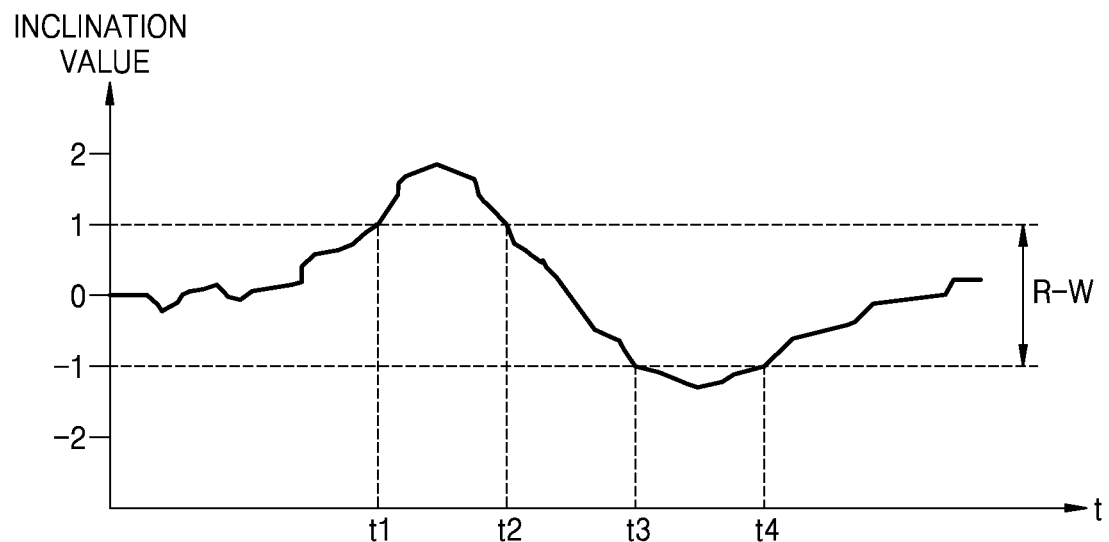
FIGS. 7A and 7B are graphs showing changes in an inclination value of a torch.
Figure 7B:
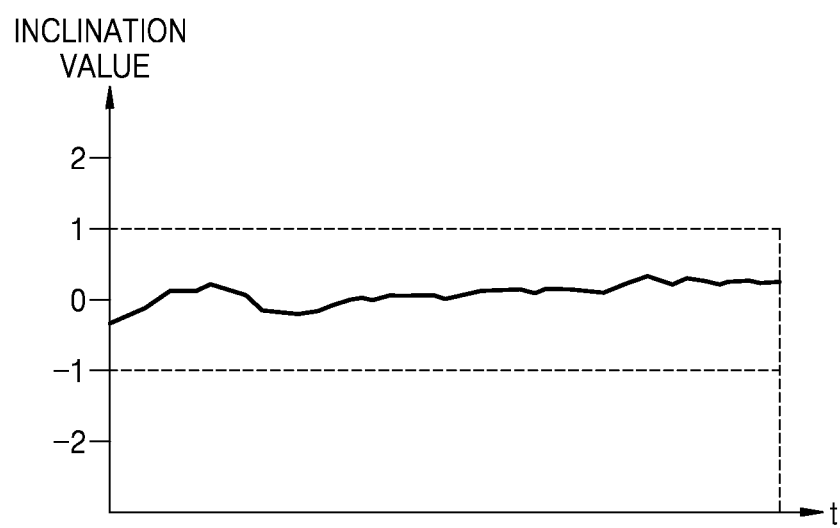

FIGS. 7A and 7B are graphs showing changes in an inclination value of a torch.

As illustrated in FIG. 7A, inclination values of a torch may be received. The status alarm mask 100 may display the received inclination values of the torch over time. The status alarm mask 100 may set an inclination value of a torch, which has been input in a setting mode, to 0, and may set values corresponding to 10% of the inclination value of the torch as a normal range (R-W). The normal range may be a range between values of −10% and +10% of the inclination value of the torch.

Referring to FIG. 7A, first notification output data may be generated during a first time interval between t1 and t2 and a second time interval between t3 and t4. When the first time interval exceeds a first preset time, the first notification output data may be converted into the second notification output data and provided at the time when the first time elapses from the time point t1. In addition, at the time when the first time elapses from the time point t1, a temperature of the welding torch may be lowered to a predetermined minimum temperature or less, or power of the welding torch may be cut off.

As illustrated in FIG. 7B, when the inclination value of the torch is included in the normal range during a total period of time (T) when the work is in progress, any notification output data is not output. Welding ability information of a user may be adjusted to be upgraded from previous welding ability information. Salary, allowance, and the like of a user may be increased in accordance with the upgraded welding ability information.

The above-described apparatus may be implemented as a hardware component, a software component, and/or a combination of a hardware component and a software component. For example, apparatuses and components described in the embodiments may be implemented using one or more general purpose computers or special purpose computers, for example, a processor, a controller, an arithmetic logic unit (ALU), a digital signal processor, a microcomputer, a field programmable gate array (FPGA), a programmable logic unit (PLU), a microprocessor, or any device capable of executing and responding to a command. A processing device may implement an operating system (OS) and one or more software applications implemented on the OS. In addition, the processing device may access, store, manipulate, process, and generate data in response to the execution of software. Although cases where one processing device is used have been described for convenience of understanding, it will be understood by those of ordinary skill in the art that the processing device may include a plurality of processing elements and/or a plurality of types of processing elements. For example, the processing device may include a plurality of processors or one processor and one controller. In addition, other processing configurations, such as a parallel processor, are also possible.

Software may include a computer program, code, a command, or one or more combinations thereof, and may constitute a processing device to be operated as desired or may independently or collectively command the processing device. Software and/or data may be permanently or temporarily embodied in any type of machine, component, physical device, virtual equipment, computer storage media or device, or a transmitted signal wave, in order to be interpreted by the processing device or provide a command or data to the processing device. The software may be distributed over a networked computer system to be stored or executed in a distributed manner. The software and data may be stored on one or more computer-readable recording media.

Methods according to embodiments may be implemented in a program command form which may be executed through various computer devices to be recorded on a computer-readable recording medium. The computer-readable recording medium may include a program command, a data file, data structures, and the like, either alone or in combination thereof. The program command recorded on the computer-readable recording medium may be specially designed and constructed for an embodiment, or may be known and available to those skilled in the art of computer software. An example of a computer-readable recording medium may include magnetic media such as a hard disk, a floppy disk, and magnetic tape, optical media such as compact disc read-only memory (CD-ROM) and digital versatile disc (DVD), magneto-optical media such as a floptical disk, and a hardware device specifically configured to store and execute a program command such as ROM, random access memory (RAM), a flash memory, and the like. An example of a program command may not only include a machine code generated by a compiler but also high-level language code executed by a computer using an interpreter, and the like. The hardware device described above may be configured to be operated as one or more software modules in order to perform an operation according to an embodiment, and vice versa.

As is apparent from the foregoing description of embodiments, output data corresponding to an event may be provided by monitoring an inclination value of a torch of a user and receiving an event outside a normal range.

The corresponding output data may be provided by inferring a welding status of a current work by using the inclination value of the torch.

While the present disclosure has been described with reference to example embodiments thereof and the accompanying drawings, it will be obvious to those of ordinary skill in the art that various changes and modifications are possible from the foregoing description. For example, proper results may be achieved although the above-described techniques are performed in an order different from that of the described method, and/or the above-described elements such as systems, configurations, devices, circuits, and the like are coupled or combined in a form different from that of the described method, or replaced or substituted with other elements or equivalents thereto.

Accordingly, other implementations, other embodiments, and equivalents to the claims are within the scope of the appended claims.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:
1. A status alarm mask comprising:
a main body configured to cover a face and eyes of a user;
a filter unit placed at a front surface portion of the main body and configured to protect the eyes;
a communication module configured to establish a communication session with a plurality of welding torches and receive at least one inclination value of the welding torches through the communication session;
an image sensor configured to acquire a welding image of a work done by a user holding a first welding torch of the welding torches;

a controller configured to:
  determine whether the work of the first welding torch is in progress based on the filter unit;
  determine a change in the inclination of the first welding torch by analyzing the welding image;
  when the work of the first welding torch is in progress, generate notification output data based on the change in the inclination of the first welding torch, the notification output data comprising monitoring data that has the at least one inclination value;
  monitor statuses of the plurality of welding torches by:
    determining a split time interval for each torch of the welding torches by dividing a first time interval by a total number of welding torches;
    receiving inclination values of each of the welding torches for each split time interval; and
    incorporating the received inclination values into the monitoring data; and
an output unit placed at a location not overlapping with the filter unit and configured to receive and output the notification output data.

2. The status alarm mask of claim 1, wherein the controller updates a normal range of a current work on the basis of a set of inclination values obtained at a first time interval and sets the normal range of the current work as a reference value of the current work.

3. The status alarm mask of claim 2, wherein, when a first inclination value outside the normal range is received from the welding torch, the controller generates notification output data corresponding to the first inclination value.

4. The status alarm mask of claim 1, wherein the controller is configured to generate first notification output data in accordance with a first event at which the inclination value is received during a first time period and output the first notification output data via the output unit during a second time period adjacent to the first time period, and
  the controller is configured to generate second notification output data in accordance with a second event at which the inclination value is received during the second time period and output the second notification output data via the output unit during a third time period adjacent to the second time period.

5. The status alarm mask of claim 4, wherein the first notification output data or the second notification output data is set to be output via at least one of an LED, a vibration module, and a speaker.

6. The status alarm mask of claim 1, wherein the controller is configured to generate notification output data in accordance with a first event at which the inclination value outside a normal range is received for a first period and output the notification output data via the output unit, and when an inclination value having been received for a second period is outside the normal range after the first event occurs, the controller is configured to change a temperature of the welding torch to a preset minimum temperature or less.

7. The status alarm mask of claim 1, further comprising:
receiving identification information of each of the welding torches in accordance with each split time interval; and
identifying each split time interval with a corresponding welding torch of the welding torches based on the identification information.

8. The status alarm mask of claim 1, further comprising determining welding ability information of the user based on at least one of the at least one inclination value and welding time information.

9. The status alarm mask of claim 8, further comprising changing the welding ability information based on a set of inclination values of current welding and the notification output data.

10. The status alarm mask of claim 1, wherein the statuses of the welding torches are output simultaneously.

11. The status alarm mask of claim 1, wherein the statuses of the welding torches are output sequentially.

12. A method of operating a status alarm mask, the method comprising:
  determining, whether a work of a plurality of welding torches is in progress based on a filter unit of the status alarm mask;
  determining, a change in inclination of a first welding torch of the welding torches by analyzing a welding image obtained using an image sensor of the status alarm mask;
  when the work of the first welding torch is in progress, generating notification output data based on the change in the inclination of the first welding torch, the notification output data comprising monitoring data that has at least one inclination value;
  monitoring statuses of the plurality of welding torches by:
    determining a split time interval for each torch of the welding torches by dividing a first time interval by a total number of welding torches;
    receiving inclination values of the welding torches for each split time interval; and
    incorporating the received inclination values into the monitoring data; and
  outputting the notification output data, the outputting being performed by the status alarm mask.

* * * * *